United States Patent
Huh

(10) Patent No.: US 7,564,014 B2
(45) Date of Patent: Jul. 21, 2009

(54) APPARATUS FOR DETECTING WELDING LIGHT AND PROTECTING EYES FROM GLARE AND METHOD FOR CONTROLLING THE SAME

(75) Inventor: Moon Young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 0 days.

(21) Appl. No.: 11/589,541

(22) Filed: Oct. 30, 2006

(65) Prior Publication Data
US 2007/0131845 A1 Jun. 14, 2007

(30) Foreign Application Priority Data
Dec. 14, 2005 (KR) ............... 10-2005-0123144

(51) Int. Cl.
*G01J 1/32* (2006.01)
(52) U.S. Cl. ............... 250/205; 250/201.1; 250/214 B; 250/214 AL; 349/14; 2/8.1; 219/147; 359/601; 359/604
(58) Field of Classification Search ............... 250/201.1, 250/205, 214 B, 214 AL; 349/14; 2/8.2, 2/8.3, 8.7, 8.8; 219/147; 359/601, 604
See application file for complete search history.

(56) References Cited

U.S. PATENT DOCUMENTS

| | | | | |
|---|---|---|---|---|
| 5,248,880 A | * | 9/1993 | Fergason | 250/214 B |
| 5,751,258 A | * | 5/1998 | Fergason et al. | 345/7 |
| 6,614,409 B1 | * | 9/2003 | Bae | 250/205 |
| 2005/0001155 A1 | * | 1/2005 | Fergason | 250/221 |
| 2005/0007504 A1 | * | 1/2005 | Fergason | 250/214 B |

* cited by examiner

*Primary Examiner*—Seung C Sohn
(74) *Attorney, Agent, or Firm*—Cantor Colburn LLP

(57) ABSTRACT

A welding light detection and anti-glare eye protection apparatus, which shields welding light generated in welding or cutting environments to safely protect eyes of a worker from the welding light, and a method for controlling the same are provided. When the apparatus is powered on, it is determined, based on a reference value, whether or not a specific time has passed without detecting welding light. If the specific time has passed without detecting welding light, a power saving mode is performed. If welding light is detected while the power saving mode is performed, normal power is supplied and light transmittance is controlled. When the power saving mode is performed, the reference value is reset so that photosensitivity is reduced below a specific value. This method saves energy while preventing the apparatus from operating abnormally. Thus, it is possible to drive the anti-glare eye protection plate most efficiently according to ambient environments.

1 Claim, 3 Drawing Sheets

APPARATUS FOR DETECTING WELDING LIGHT AND PROTECTING EYES FROM GLARE AND METHOD FOR CONTROLLING THE SAME

BACKGROUND OF THE INVENTION

1. Field of the Invention

The present invention relates to an anti-glare eye protection apparatus, and more particularly to an apparatus for detecting welding light and protecting eyes from glare, which shields welding light generated in a welding or cutting environment to safely protect eyes of a worker from the welding light, and a method for controlling the apparatus.

2. Description of the Related Art

Generally, workers use a welding light detection and anti-glare eye protection apparatus placed on their head to adjust the intensity of light generated by a welding or cutting torch which enters their eyes.

FIG. 1 is a perspective view of a protection mask having a conventional anti-glare eye protection apparatus.

As shown in FIG. 1, a protection mask 1 having an anti-glare eye protection apparatus 2 and solar cell 3 mounted at a front portion of the protection mask 1 reduces the intensity of light entering eyes of a worker through an anti-glare eye protection plate 5 which is a liquid crystal display (LCD) included in the anti-glare eye protection apparatus 2.

More specifically, a photosensor 4 such as a photodiode provided on the anti-glare eye protection apparatus 2 at a front portion thereof senses light generated by the welding or cutting torch. Based on the detected light, a control circuit included in the anti-glare eye protection apparatus 2 controls the anti-glare eye protection plate 5 to be darkened so that the intensity of light passing through the anti-glare eye protection plate 5 is reduced, thereby protecting eyes of the worker who wears the protection mask 1.

However, the conventional welding light detection and anti-glare eye protection apparatus has the following problem. To conduct welding, first, the worker must power the apparatus on. When a specific time has passed after the power of the apparatus is turned on, the power is turned off automatically regardless of whether or not welding light is present. Thus, the worker may be exposed to strong welding light by starting welding without knowing that the power was turned off.

If workers are directly exposed to welding light by conducting welding without knowing that the apparatus is off, they may suffer from tired eyes and get eye diseases, thus increasing the occurrence of work-related industrial accidents.

SUMMARY OF THE INVENTION

Therefore, the present invention has been made in view of the above problems, and it is an object of the present invention to provide an apparatus for detecting welding light and protecting eyes from glare and a method for controlling the apparatus, wherein a power supply is switched to a power saving mode when no task has been conducted for a specific time after power is turned on and the power supply again supplies normal power to control light transmittance to be reduced when welding light is detected.

In accordance with one aspect of the present invention, the above and other objects can be accomplished by the provision of an apparatus for detecting welding light and protecting eyes from glare, the apparatus comprising an anti-glare eye protection plate for protecting eyes of a worker from light generated by a welding or cutting torch; a power supply controller for allowing a power supply to supply power in a normal power mode or switching the power supply to a power saving mode; a light detector for detecting welding light based on a signal received from a photosensor; a photosensitivity controller for setting a reference value for adjusting detection sensitivity of the light detector; a main controller for switching the power supply to the power saving mode through the power supply controller when a specific time has passed without detecting welding light after the apparatus is powered on, monitoring changes in a received light intensity using an output of the light detector, and allowing the intensity of transmitted welding light to be reduced below a specific level through a light transmittance controller when the received light intensity is equal to or higher than a preset reference value and thus it is determined that welding light has been detected; and a light transmittance controller for driving the anti-glare eye protection plate under control of the main controller to control light transmittance of the anti-glare eye protection plate.

Preferably, when the power saving mode is performed, the main controller resets the reference value of the photosensitivity controller so that photosensitivity is reduced below a specific value.

In accordance with another aspect of the present invention, there is provided a method for controlling an apparatus for detecting welding light and protecting eyes from glare, the apparatus including an anti-glare eye protection plate for protecting eyes of a worker from light generated by a welding or cutting torch, the method comprising determining, when the apparatus is powered on, whether or not a specific time has passed without detecting welding light, based on a reference value; performing a power saving mode if the specific time has passed without detecting welding light; and supplying normal power and controlling light transmittance if welding light has been detected while the power saving mode is performed.

Preferably, when the power saving mode is performed, the reference value is reset so that photosensitivity is reduced below a specific value.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

The configuration and operation of the present invention will now be described in detail with reference to the accompanying drawings.

Figure 1:
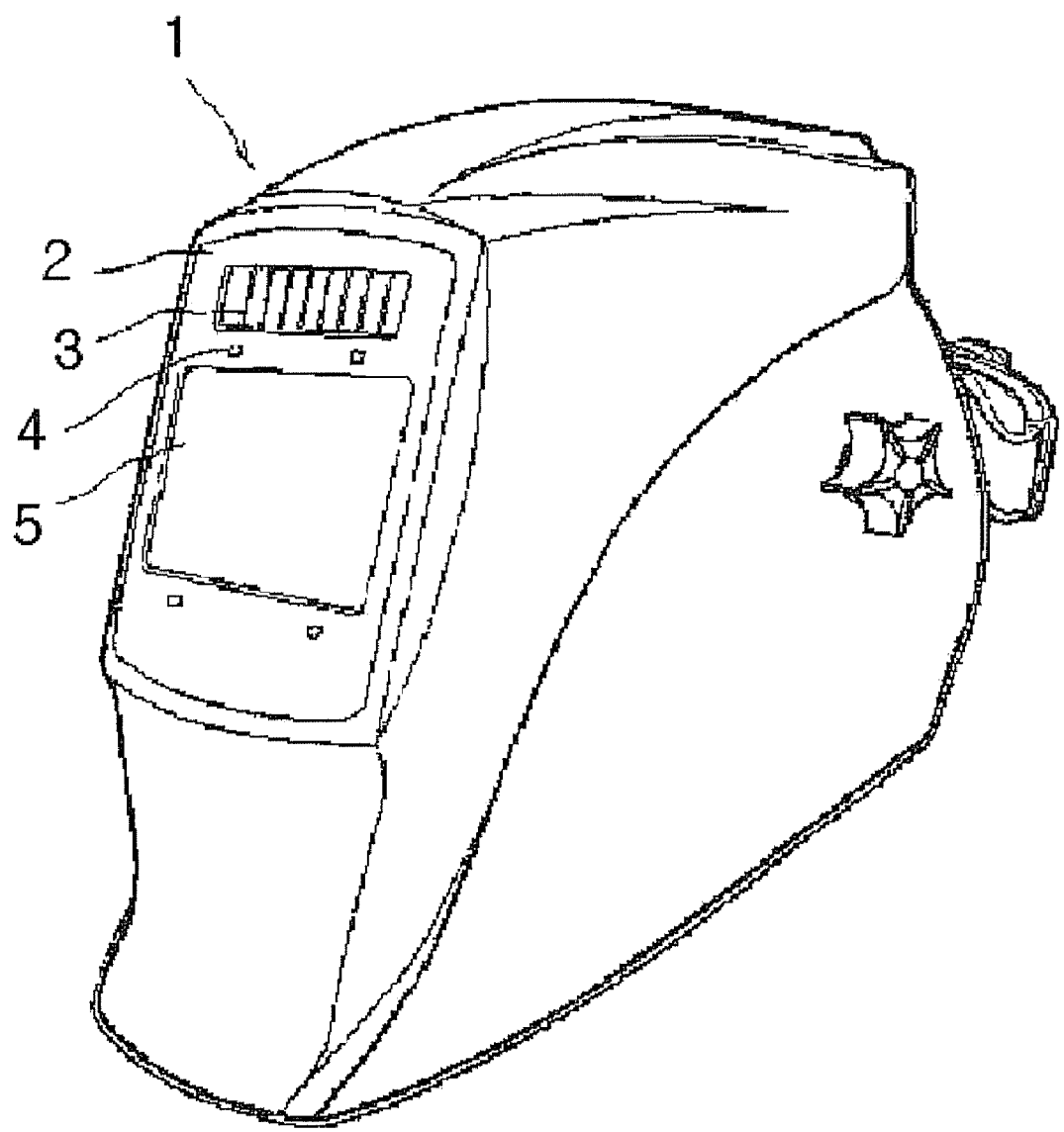
FIG. 1 is a perspective view of a protection mask having a conventional anti-glare eye protection apparatus.
Figure 2:
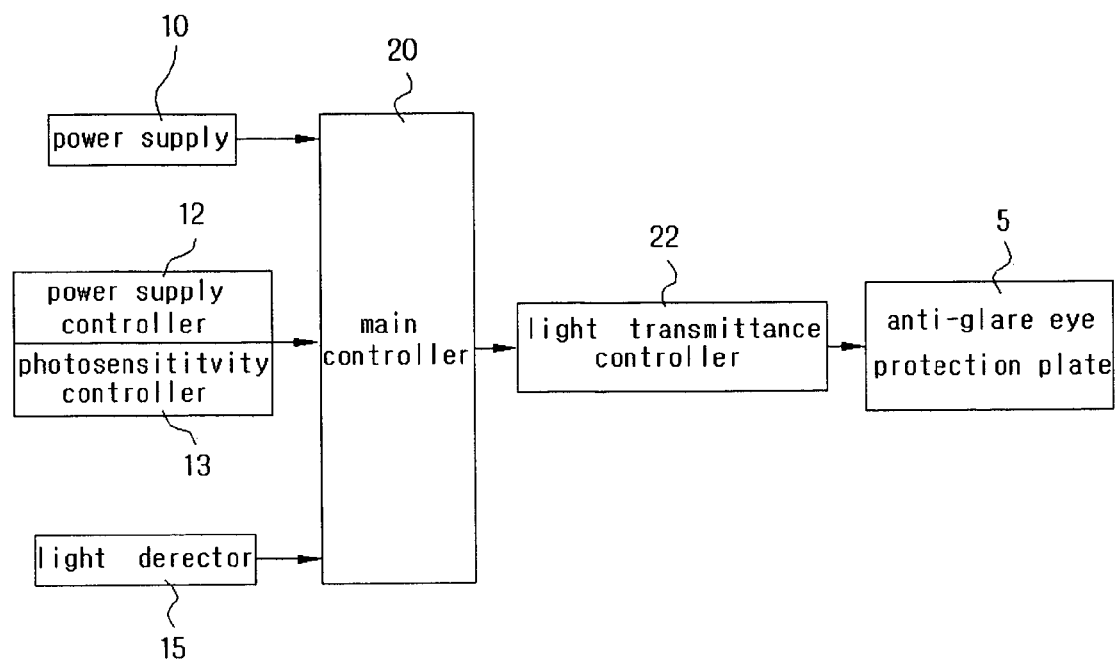
FIG. 2 is a block diagram of a welding light detection and anti-glare eye protection apparatus according to the present invention.

FIG. 2 is a block diagram of an apparatus for detecting welding light and protecting eyes from glare according to the present invention, which will hereinafter be referred to as a "welding light detection and anti-glare eye protection apparatus".

As shown in FIG. 2, the welding light detection and anti-glare eye protection apparatus according to the present invention includes a photosensor 4, an anti-glare eye protection plate 5, a power supply 10, a power supply controller 12, a photosensitivity controller 13, a light detector 15, a main controller 20, and a light transmittance controller 22.

The power supply 10 is a device that supplies power and preferably includes a battery.

The power supply controller 12 allows the power supply 10 to supply power in a normal power mode or switches the power supply 10 to a power saving mode.

The photosensitivity controller 13 sets a reference value for adjusting the detection sensitivity of the light detector 15.

The light detector 15 detects light generated by a welding or cutting torch and includes a general filter and amplifier. Specifically, the light detector 15 compares a signal received from the photosensor 4 with the reference value set by the photosensitivity controller 13 and detects a change in the light intensity.

When a specific time has passed without detecting welding light after the power is turned on, the main controller 20 switches the power supply 10 to the power saving mode through the power supply controller 12 and monitors changes in the received light intensity using an output of the light detector 15. When the received light intensity has exceeded the preset reference value and thus it is determined that welding light has been detected, the main controller 20 allows the intensity of transmitted welding light to be reduced below a specific level through the light transmittance controller 22. To accomplish this, the main controller 20 preferably includes a microcomputer.

The light transmittance controller 22 can drive the anti-glare eye protection plate 5 under the control of the main controller 20 to control the light transmittance of the anti-glare eye protection plate 5. Specifically, when the received light intensity has exceeded the preset reference value, the light transmittance controller 22 is activated to control the light transmittance of the anti-glare eye protection plate 5 according to an output signal of the main controller 20.

Figure 3:
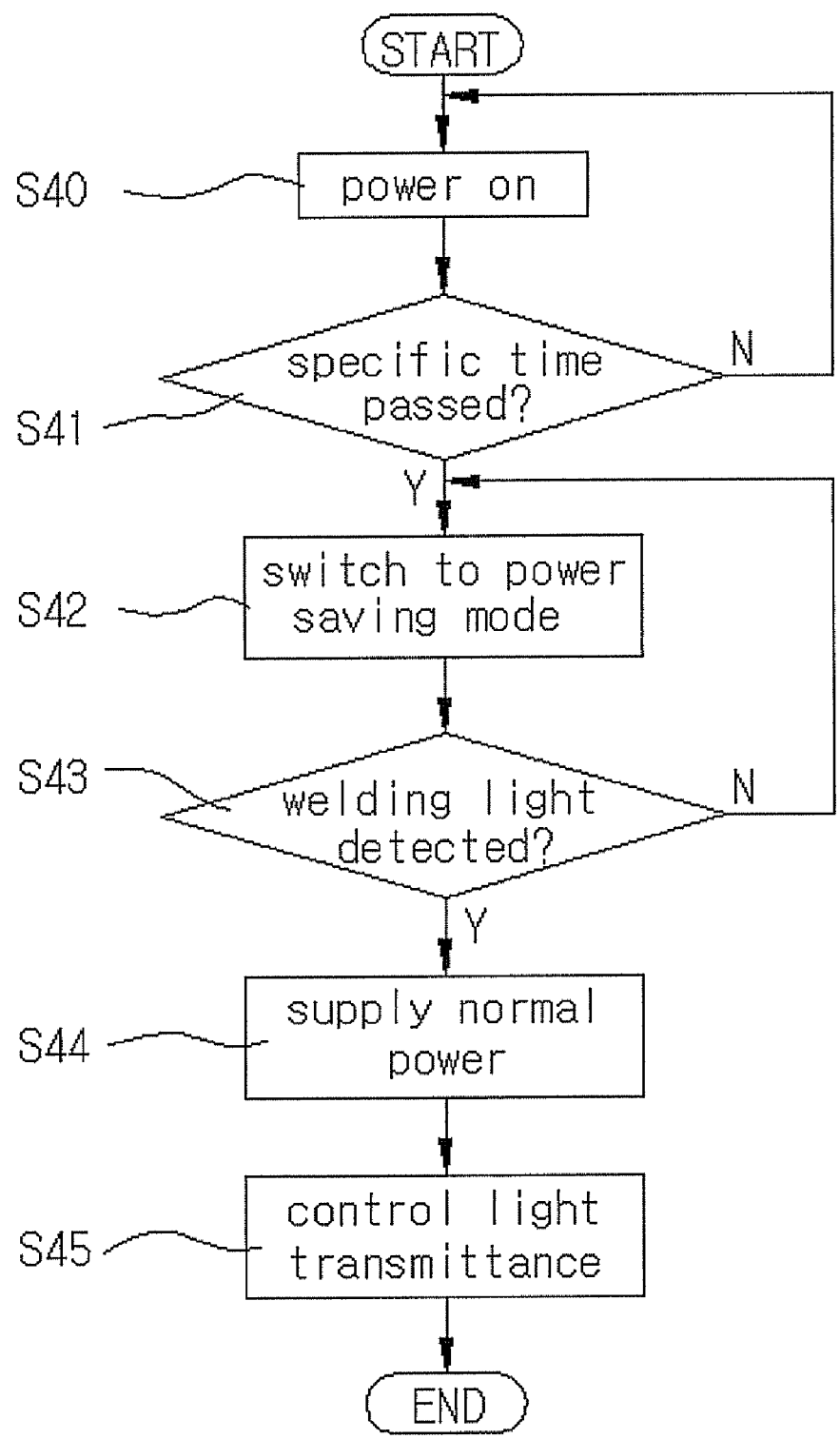
FIG. 3 is a flow chart of a method for controlling the welding light detection and anti-glare eye protection apparatus according to the present invention.

FIG. 3 is a flow chart of a method for controlling the welding light detection and anti-glare eye protection apparatus according to the present invention.

The method for controlling the welding light detection and anti-glare eye protection apparatus according to the present invention includes determining, when power is on, whether or not a specific time has passed without detecting welding light (S40-S41), performing a power saving mode if the specific time has passed without detecting welding light (S41-S42), and supplying normal power and controlling light transmittance if welding light has been detected while the power saving mode is performed (S43-S45).

The welding light detection and anti-glare eye protection apparatus constructed as described above and the method for controlling the welding light detection and anti-glare eye protection apparatus according to the present invention will now be described in more detail.

When power is on, the power supply controller 12 activates a power saving mode if a specific time has passed in which the light detector 15 detects no change in the intensity of light generated by a welding or cutting torch (S40-S42).

More specifically, the light detector 15 detects a change in the intensity of the light by comparing a signal received from the photosensor 4 with the reference value set by the photosensitivity controller 13. Here, when a specific time has passed without detecting welding light after the power is turned on, the main controller 20 switches the power supply 10 to the power saving mode through the power supply controller 12 and monitors changes in the received light intensity using the output of the light detector 15.

If welding light has been detected while the power saving mode is performed, the main controller 20 performs steps S43-S45 to supply normal power and to control light transmittance.

When the received light intensity has exceeded the preset reference value and thus it is determined that welding light has been detected, the main controller 20 reduces the intensity of transmitted welding light below a specific level through the light transmittance controller 22.

The light transmittance controller 22 drives the anti-glare eye protection plate 5 under the control of the main controller 20. When the received light intensity has exceeded the preset reference value, the light transmittance controller 22 controls the light transmittance of the anti-glare eye protection plate 5 according to an output signal of the main controller 20.

When the power saving mode is performed, the main controller 22 resets the reference value of the photosensitivity controller 13 so that the photosensitivity is reduced below a specific value. This allows the apparatus to consume minimum operating power while preventing the apparatus from operating abnormally by incident light with less than a specific light intensity in lux.

As is apparent from the above description, the present invention provides an apparatus for detecting welding light and protecting eyes from glare and a method for controlling the same which have a variety of advantages. For example, the power supply is switched to a power saving mode when no task has been conducted for a specific time after power is turned on and the power supply again supplies normal power to control light transmittance to be reduced when welding light is detected. This saves energy while preventing the apparatus from operating abnormally. Thus, it is possible to drive the anti-glare eye protection plate most efficiently according to ambient environments.

In addition, while the conventional apparatus requires that the worker turn on the power to start welding, the apparatus according to the present invention is automatically powered on when the worker conducts welding so that the worker is not exposed to strong welding light, thereby preventing the worker from suffering from tired eyes and getting eye diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for controlling an apparatus for detecting welding light and protecting eyes from glare, the apparatus including an anti-glare eye protection plate for protecting eyes of a worker from light generated by a welding or cutting torch, the method comprising:

determining, when the apparatus is powered on, whether a specific time has passed without detecting welding light, based on a reference value;

performing a power saving mode if the specific time has passed without detecting the welding light; and supplying normal power and controlling light transmittance of the anti-glare eye protection plate if the welding light has been detected while the power saving mode is performed, wherein, when the power saving mode is performed, the reference value is reset so that photosensitivity is reduced below a specific value.

* * * * *